United States Patent
Hawkes et al.

(10) Patent No.: US 8,097,025 B2
(45) Date of Patent: *Jan. 17, 2012

(54) PEDICLE SCREW SYSTEM CONFIGURED TO RECEIVE A STRAIGHT OR CURVED ROD

(75) Inventors: David T. Hawkes, Pleasant Grove, UT (US); David R. Warnick, Spanish Fork, UT (US); Michael D. Ensign, Salt Lake City, UT (US); Thomas M. Sweeney, Sarasota, FL (US)

(73) Assignee: X-spine Systems, Inc., Miamisburg, OH (US)

( * ) Notice: Subject to any disclaimer, the term of this patent is extended or adjusted under 35 U.S.C. 154(b) by 869 days.

This patent is subject to a terminal disclaimer.

(21) Appl. No.: 12/056,571

(22) Filed: Mar. 27, 2008

(65) Prior Publication Data

US 2008/0249576 A1    Oct. 9, 2008

Related U.S. Application Data

(63) Continuation-in-part of application No. 11/327,132, filed on Jan. 6, 2006, now Pat. No. 7,604,655, which is a continuation-in-part of application No. 11/258,831, filed on Oct. 25, 2005, now Pat. No. 7,662,172.

(60) Provisional application No. 60/920,222, filed on Mar. 27, 2007.

(51) Int. Cl.
*A61B 17/70* (2006.01)

(52) U.S. Cl. ......... 606/269; 606/264; 606/265; 606/308

(58) Field of Classification Search .......... 606/250–253, 606/264–272, 278, 300, 301, 305–308
See application file for complete search history.

(56) References Cited

U.S. PATENT DOCUMENTS

| 483,342 | A | 9/1892 | Bolte |
| 900,717 | A | 10/1908 | Feaster |

(Continued)

FOREIGN PATENT DOCUMENTS

DE    3219575 A1    12/1983

(Continued)

OTHER PUBLICATIONS

Expedium Spine System, DePuy Spine, Raynham, MA 02767.

(Continued)

*Primary Examiner* — Eduardo C Robert
*Assistant Examiner* — Ellen C Hammond
(74) *Attorney, Agent, or Firm* — Jacox, Meckstroth & Jenkins

(57) ABSTRACT

A fastener and a bone fixation assembly for the internal fixation of vertebral bodies such as a pedicle screw is provided which allows a detachable tulip to be provisionally locked to a pedicle screw in a first position, while securely locking the tulip assembly to the pedicle screw when in a second position. According to one exemplary embodiment, the tulip assembly includes a tulip body, a coupling saddle, and an expansion ring serving as a fastener. The fastener secures the tulip body to the pedicle screw, while the coupling saddle provides a means to provisionally lock the tulip body at an angle relative to the pedicle screw via an interference fit. Incline planes on the walls of the tulip body provide means to rotationally lock a rod within the tulip assembly, and fully lock the tulip assembly to at an angle relative to the pedicle screw.

16 Claims, 9 Drawing Sheets

U.S. PATENT DOCUMENTS

| | | | |
|---|---|---|---|
| 920,188 A | 5/1909 | Schumacher | |
| 1,171,380 A | 2/1916 | Arthur | |
| 1,536,559 A | 5/1925 | Carroll | |
| 2,344,381 A | 3/1944 | Young | |
| 3,019,504 A | 2/1962 | Castagliuolo | |
| 3,648,691 A | 3/1972 | Lumb et al. | |
| 3,752,203 A | 8/1973 | Hill, Jr. | |
| 3,851,601 A | 12/1974 | Davis | |
| 3,875,936 A | 4/1975 | Volz | |
| 4,011,602 A | 3/1977 | Rybicki et al. | |
| 4,085,744 A | 4/1978 | Lewis et al. | |
| 4,269,178 A | 5/1981 | Keene | |
| 4,289,124 A | 9/1981 | Zickel | |
| 4,294,300 A | 10/1981 | Bouwman | |
| 4,309,139 A | 1/1982 | Nakae | |
| 4,411,259 A | 10/1983 | Drummond | |
| 4,604,995 A | 8/1986 | Stephens et al. | |
| 4,611,580 A | 9/1986 | Wu | |
| 4,611,581 A | 9/1986 | Steffee | |
| 4,641,636 A | 2/1987 | Cotrel | |
| 4,648,388 A | 3/1987 | Steffee | |
| 4,653,481 A | 3/1987 | Howland et al. | |
| 4,655,199 A | 4/1987 | Steffee | |
| 4,658,809 A | 4/1987 | Ulrich et al. | |
| 4,696,290 A | 9/1987 | Steffee | |
| 4,719,905 A | 1/1988 | Steffee | |
| 4,763,644 A | 8/1988 | Webb | |
| 4,771,767 A | 9/1988 | Steffee | |
| 4,805,602 A | 2/1989 | Puno et al. | |
| 4,815,453 A | 3/1989 | Cotrel | |
| 4,887,595 A | 12/1989 | Heinig et al. | |
| 4,887,596 A | 12/1989 | Sherman | |
| 4,913,134 A | 4/1990 | Luque | |
| 4,946,458 A | 8/1990 | Harms et al. | |
| 4,950,269 A | 8/1990 | Gaines | |
| 5,005,562 A | 4/1991 | Cotrel | |
| 5,024,213 A | 6/1991 | Asher et al. | |
| 5,042,982 A | 8/1991 | Harms et al. | |
| 5,067,955 A | 11/1991 | Cotrel | |
| 5,084,049 A | 1/1992 | Asher et al. | |
| 5,092,867 A | 3/1992 | Harms et al. | |
| 5,113,685 A | 5/1992 | Asher et al. | |
| 5,120,171 A | 6/1992 | Lasner | |
| 5,127,912 A | 7/1992 | Ray et al. | |
| 5,129,900 A | 7/1992 | Asher et al. | |
| 5,154,719 A * | 10/1992 | Cotrel | 606/308 |
| 5,176,680 A | 1/1993 | Vignaud et al. | |
| 5,183,359 A | 2/1993 | Barth | |
| 5,190,543 A | 3/1993 | Schlapfer | |
| 5,196,013 A | 3/1993 | Harms et al. | |
| 5,207,678 A | 5/1993 | Harms et al. | |
| 5,246,303 A | 9/1993 | Trilla et al. | |
| 5,257,993 A | 11/1993 | Asher et al. | |
| 5,261,913 A | 11/1993 | Marnay | |
| 5,312,402 A | 5/1994 | Schlapfer | |
| 5,346,493 A | 9/1994 | Stahurski et al. | |
| 5,360,431 A | 11/1994 | Puno | |
| 5,380,325 A | 1/1995 | Lahille et al. | |
| 5,443,467 A | 8/1995 | Biedermann et al. | |
| 5,466,237 A | 11/1995 | Byrd et al. | |
| 5,474,555 A | 12/1995 | Puno et al. | |
| 5,520,689 A | 5/1996 | Schlapfer | |
| 5,534,001 A | 7/1996 | Schlapfer et al. | |
| 5,549,608 A | 8/1996 | Errico et al. | |
| 5,562,663 A | 10/1996 | Wisnewski et al. | |
| 5,603,714 A | 2/1997 | Kaneda et al. | |
| 5,609,593 A | 3/1997 | Errico et al. | |
| 5,624,442 A | 4/1997 | Mellinger et al. | |
| 5,647,873 A | 7/1997 | Errico et al. | |
| 5,667,508 A | 9/1997 | Errico et al. | |
| 5,669,911 A | 9/1997 | Errico et al. | |
| 5,690,630 A | 11/1997 | Errico et al. | |
| 5,733,285 A | 3/1998 | Errico et al. | |
| 5,797,911 A | 8/1998 | Sherman et al. | |
| 5,817,094 A | 10/1998 | Errico et al. | |
| 5,879,350 A | 3/1999 | Sherman | |
| 5,882,350 A | 3/1999 | Ralph | |
| 5,885,286 A | 3/1999 | Sherman et al. | |
| 5,891,145 A | 4/1999 | Morrison et al. | |
| 5,954,725 A | 9/1999 | Sherman | |
| 6,010,503 A | 1/2000 | Richelsoph | |
| 6,063,090 A | 5/2000 | Schlapfer | |
| 6,077,262 A * | 6/2000 | Schlapfer et al. | 606/305 |
| 6,090,111 A | 7/2000 | Nichols | |
| 6,113,601 A | 9/2000 | Tatar | |
| 6,132,432 A | 10/2000 | Richelsoph | |
| 6,235,033 B1 | 5/2001 | Brace et al. | |
| 6,280,442 B1 | 8/2001 | Baker et al. | |
| 6,302,888 B1 | 10/2001 | Mellinger et al. | |
| RE37,665 E | 4/2002 | Ralph | |
| 6,371,957 B1 | 4/2002 | Amrein et al. | |
| 6,402,752 B2 | 6/2002 | Schaffler-Wachter | |
| 6,451,021 B1 | 9/2002 | Ralph | |
| 6,475,218 B2 | 11/2002 | Gournay et al. | |
| 6,488,681 B2 | 12/2002 | Martin et al. | |
| 6,520,963 B1 | 2/2003 | McKinley | |
| 6,623,485 B2 | 9/2003 | Doubler et al. | |
| 6,626,908 B2 | 9/2003 | Cooper et al. | |
| 6,652,526 B1 | 11/2003 | Arafiles | |
| 6,660,004 B2 | 12/2003 | Barker et al. | |
| 6,716,214 B1 | 4/2004 | Jackson | |
| 6,730,089 B2 | 5/2004 | Jackson | |
| 6,730,093 B2 | 5/2004 | Saint Martin | |
| 6,755,829 B1 | 6/2004 | Bono et al. | |
| 6,786,903 B2 | 9/2004 | Lin | |
| 6,793,657 B2 | 9/2004 | Lee et al. | |
| 6,802,844 B2 | 10/2004 | Ferree | |
| 6,827,719 B2 | 12/2004 | Ralph | |
| 6,840,940 B2 | 1/2005 | Ralph | |
| 6,843,791 B2 | 1/2005 | Serhan | |
| 6,858,030 B2 | 2/2005 | Martin et al. | |
| 6,863,464 B1 | 3/2005 | Niklaus | |
| 6,869,433 B2 | 3/2005 | Glascott | |
| 6,896,677 B1 | 5/2005 | Lin | |
| 7,022,122 B2 | 4/2006 | Amrein | |
| 7,081,117 B2 | 7/2006 | Bono et al. | |
| 7,083,621 B2 | 8/2006 | Shaolian et al. | |
| 7,090,674 B2 | 8/2006 | Doubler et al. | |
| 7,125,426 B2 | 10/2006 | Moumene et al. | |
| 7,141,051 B2 | 11/2006 | Janowski et al. | |
| 7,261,715 B2 | 8/2007 | Rezach et al. | |
| 7,291,151 B2 | 11/2007 | Alvarez | |
| 7,291,153 B2 | 11/2007 | Glascott | |
| 7,294,128 B2 | 11/2007 | Alleyne et al. | |
| 7,322,981 B2 | 1/2008 | Jackson | |
| 7,338,491 B2 | 3/2008 | Baker et al. | |
| 7,377,923 B2 | 5/2008 | Purcell et al. | |
| 7,524,325 B2 * | 4/2009 | Khalili | 606/290 |
| 7,625,394 B2 | 12/2009 | Molz, IV et al. | |
| 7,657,960 B2 | 2/2010 | Umbrell | |
| 7,682,377 B2 | 3/2010 | Konieczynski et al. | |
| 7,766,946 B2 * | 8/2010 | Bailly | 606/267 |
| 2002/0013585 A1 | 1/2002 | Gournay et al. | |
| 2002/0026193 A1 | 2/2002 | Barker et al. | |
| 2002/0082601 A1 | 6/2002 | Toyama et al. | |
| 2002/0091386 A1 | 7/2002 | Martin et al. | |
| 2002/0111626 A1 | 8/2002 | Ralph et al. | |
| 2002/0120272 A1 | 8/2002 | Yuan et al. | |
| 2002/0133154 A1 | 9/2002 | Saint Martin | |
| 2002/0133158 A1 | 9/2002 | Saint Martin | |
| 2002/0143341 A1 * | 10/2002 | Biedermann et al. | 606/73 |
| 2002/0151900 A1 | 10/2002 | Glascott | |
| 2002/0183748 A1 | 12/2002 | Martin et al. | |
| 2003/0032957 A1 | 2/2003 | McKinley | |
| 2003/0073996 A1 | 4/2003 | Doubler et al. | |
| 2003/0078583 A1 | 4/2003 | Biedermann et al. | |
| 2003/0187433 A1 | 10/2003 | Lin | |
| 2003/0187434 A1 | 10/2003 | Lin | |
| 2003/0199873 A1 | 10/2003 | Richelsoph | |
| 2003/0231927 A1 | 12/2003 | Hale | |
| 2004/0039383 A1 | 2/2004 | Jackson | |
| 2004/0039384 A1 | 2/2004 | Boehm | |
| 2004/0049190 A1 | 3/2004 | Biedermann | |
| 2004/0097933 A1 | 5/2004 | Lourdel et al. | |
| 2004/0116929 A1 * | 6/2004 | Barker et al. | 606/61 |
| 2004/0127896 A1 | 7/2004 | Lombardo et al. | |
| 2004/0138662 A1 | 7/2004 | Landry et al. | |

| | | |
|---|---|---|
| 2004/0153068 A1 | 8/2004 | Janowski et al. |
| 2004/0172020 A1 | 9/2004 | Beaurain et al. |
| 2004/0172022 A1 | 9/2004 | Landry et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0033296 A1 | 2/2005 | Bono et al. |
| 2005/0049589 A1 | 3/2005 | Jackson |
| 2005/0096653 A1 | 5/2005 | Doubler et al. |
| 2005/0113830 A1 | 5/2005 | Rezach et al. |
| 2005/0131410 A1 | 6/2005 | Lin |
| 2005/0177154 A1 | 8/2005 | Moumene et al. |
| 2005/0177157 A1 | 8/2005 | Jahng |
| 2005/0182400 A1 | 8/2005 | White |
| 2005/0187548 A1* | 8/2005 | Butler et al. ............ 606/61 |
| 2005/0192570 A1 | 9/2005 | Jackson |
| 2005/0192571 A1 | 9/2005 | Abdelgany |
| 2005/0192573 A1 | 9/2005 | Abdelgany |
| 2005/0203515 A1 | 9/2005 | Doherty et al. |
| 2005/0203516 A1 | 9/2005 | Biedermann et al. |
| 2005/0203519 A1 | 9/2005 | Harms et al. |
| 2005/0215998 A1 | 9/2005 | Donath |
| 2005/0215999 A1 | 9/2005 | Birkmeyer et al. |
| 2005/0216003 A1 | 9/2005 | Biedermann et al. |
| 2005/0216004 A1 | 9/2005 | Schwab |
| 2005/0222570 A1 | 10/2005 | Jackson |
| 2005/0240180 A1 | 10/2005 | Vienney et al. |
| 2005/0261687 A1 | 11/2005 | Garamszegi et al. |
| 2006/0025767 A1* | 2/2006 | Khalili ............ 606/61 |
| 2006/0025771 A1 | 2/2006 | Jackson |
| 2006/0069391 A1 | 3/2006 | Jackson |
| 2006/0084982 A1 | 4/2006 | Kim |
| 2006/0084984 A1 | 4/2006 | Kim |
| 2006/0084987 A1 | 4/2006 | Kim |
| 2006/0089644 A1 | 4/2006 | Felix |
| 2006/0100621 A1 | 5/2006 | Jackson |
| 2006/0100622 A1 | 5/2006 | Jackson |
| 2006/0111712 A1 | 5/2006 | Jackson |
| 2006/0111715 A1 | 5/2006 | Jackson |
| 2006/0129147 A1 | 6/2006 | Biedermann et al. |
| 2006/0129149 A1 | 6/2006 | Iott et al. |
| 2006/0142760 A1 | 6/2006 | McDonnell |
| 2006/0155278 A1 | 7/2006 | Warnick |
| 2006/0161152 A1 | 7/2006 | Ensign et al. |
| 2006/0161153 A1 | 7/2006 | Hawkes et al. |
| 2006/0173456 A1 | 8/2006 | Hawkes et al. |
| 2006/0195086 A1 | 8/2006 | Sybert |
| 2006/0200128 A1 | 9/2006 | Mueller |
| 2006/0217716 A1 | 9/2006 | Baker et al. |
| 2006/0229615 A1 | 10/2006 | Abdou |
| 2006/0235392 A1 | 10/2006 | Hammer et al. |
| 2006/0235393 A1 | 10/2006 | Bono et al. |
| 2006/0241603 A1* | 10/2006 | Jackson ............ 606/61 |
| 2006/0264933 A1 | 11/2006 | Baker et al. |
| 2006/0276792 A1 | 12/2006 | Ensign et al. |
| 2006/0293659 A1 | 12/2006 | Alvarez |
| 2006/0293664 A1 | 12/2006 | Schumacher |
| 2007/0043357 A1* | 2/2007 | Kirschman ............ 606/61 |
| 2007/0043359 A1 | 2/2007 | Altarac et al. |
| 2007/0053765 A1 | 3/2007 | Warnick et al. |
| 2007/0055242 A1 | 3/2007 | Bailly |
| 2007/0090238 A1 | 4/2007 | Justis |
| 2007/0093817 A1 | 4/2007 | Barrus et al. |
| 2007/0093821 A1 | 4/2007 | Freudiger |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0093832 A1 | 4/2007 | Abdelgany |
| 2007/0100341 A1 | 5/2007 | Reglos et al. |
| 2007/0123862 A1 | 5/2007 | Warnick |
| 2007/0123867 A1 | 5/2007 | Kirschman |
| 2007/0162008 A1 | 7/2007 | Cline, Jr. et al. |
| 2007/0167949 A1 | 7/2007 | Altarac et al. |
| 2007/0173819 A1 | 7/2007 | Sandlin |
| 2007/0239159 A1 | 10/2007 | Altarac et al. |
| 2007/0288004 A1 | 12/2007 | Alvarez |
| 2007/0293861 A1 | 12/2007 | Rezach et al. |
| 2008/0004625 A1 | 1/2008 | Runco et al. |
| 2008/0039839 A1 | 2/2008 | Songer et al. |
| 2008/0039840 A1 | 2/2008 | Songer et al. |
| 2008/0045953 A1 | 2/2008 | Garamszegi |
| 2008/0045956 A1 | 2/2008 | Songer et al. |
| 2008/0071277 A1 | 3/2008 | Warnick |
| 2008/0086131 A1 | 4/2008 | Daly et al. |
| 2008/0097441 A1 | 4/2008 | Hayes et al. |
| 2008/0097457 A1 | 4/2008 | Warnick |
| 2008/0167689 A1 | 7/2008 | Matthis et al. |

FOREIGN PATENT DOCUMENTS

| | | |
|---|---|---|
| DE | 3639810 A1 | 5/1988 |
| DE | 3711013 C1 | 6/1988 |
| DE | 9403231 U1 | 4/1994 |
| EP | 128058 A1 | 12/1984 |
| EP | 242705 A2 | 10/1987 |
| EP | 242708 A2 | 10/1987 |
| EP | 1190678 A2 | 3/2002 |
| EP | 1210914 A1 | 5/2002 |
| EP | 1604617 A1 | 12/2005 |
| FR | 2615095 A1 | 11/1988 |
| FR | 2624720 A1 | 6/1989 |
| FR | 2706762 A1 | 12/1994 |
| FR | 2852815 A1 | 10/2004 |
| GB | 167228 A | 7/1921 |
| GB | 2173104 A | 10/1986 |
| WO | 8707134 A1 | 12/1987 |
| WO | 0036308 A1 | 6/2000 |
| WO | 01/52758 A1 | 6/2001 |
| WO | 02/080788 A1 | 10/2002 |
| WO | 03/086204 A2 | 4/2003 |
| WO | 2004/103194 A1 | 5/2004 |
| WO | 2004/089245 A2 | 10/2004 |
| WO | 2006/047555 A2 | 5/2006 |
| WO | 2006/047707 A2 | 5/2006 |
| WO | 2006/047711 A2 | 5/2006 |
| WO | 2007075454 A1 | 7/2007 |
| WO | 2008008511 A2 | 1/2008 |

OTHER PUBLICATIONS

The X-Spine Capless Pedicle Screw System, X-spine Systems, Inc., Miamisburg, Ohio 45342; Admitted Prior Art As to New Matter Only.

* cited by examiner

PEDICLE SCREW SYSTEM CONFIGURED TO RECEIVE A STRAIGHT OR CURVED ROD

RELATED APPLICATIONS

The present application is a continuation-in-part of U.S. patent application Ser. No. 11/327,132 filed Jan. 6, 2006 now U.S. Pat. No. 7,604,655 and titled "Bone Fixation System and Method for Using the Same" which application is a continuation-in-part of U.S. patent application Ser. No. 11/258,831 titled "Pedicle Screw Systems and Methods of Assembling/installing the Same" filed on Oct. 25, 2005 now U.S. Pat. No. 7,662,172. Additionally, the present application claims the benefit under 35 U.S.C § 119(e) of U.S. Provisional Patent Application No. 60/920,222 filed Mar. 27, 2007 titled "Masterlock Pedicle Screw System Configured to Receive a Straight or Curved Rod". The afore mentioned applications are incorporated herein by reference in their entireties.

FIELD

The present system and method relate to bone fixation devices. More particularly, the present system and method provide for a screw assembly configured to facilitate the internal fixation of vertebral bodies through the use of a pedicle screw and an attached rod.

BACKGROUND

Various devices for internal fixation of bone segments in the human or animal body are known in the art. One type of system is a pedicle screw system, which may be used as an adjunct to spinal fusion surgery, and which provides a means of gripping a spinal segment. This is particularly used within the fields of orthopedic surgery and neurosurgery, in which spinal implants and rods hold vertebral members in position relative to one another.

The spinal column is a highly complex structure that not only allows a degree of flexible movement in many directions, but also serves to cover and protect veins, arteries, and nerves essential to the body. The adult human spine contains more than twenty discrete bones coupled to one another through posterior facet joints and cartilage. Adjacent muscles coordinate movement in many directions. Various systems have been designed with the intent to provide the vertebrae immobilization when needed for the repair of damaged portions of the spine. Typical spinal fixation devices are implanted in the spine or spinal column and are classified as anterior, posterior, or lateral implants. Of particular interest, rod assemblies may be used as a spinal fixation device and generally include pedicle screws securing rods between various vertebrae.

A conventional pedicle screw system includes a pedicle screw, a rod-receiving device, and a rod. The pedicle screw includes an externally threaded stem and a head portion. The rod-receiving device is coupled to the head portion of the pedicle screw after insertion of the pedicle screw. Subsequently, the rod-receiving device securely receives a rod (commonly referred to as a distraction rod). Two such systems are inserted into respective vertebrae and adjusted to distract and/or stabilize a spinal column, for instance during an operation to correct a herniated disk, by one or more rods. The pedicle screw does not, by itself, fixate the spinal segment, but rather operates as an anchor point to receive the rod-receiving device, which in turn receives the rod. One goal of such a system is to substantially reduce and/or prevent relative motion between the spinal segments that are being fused.

When placing the rod in a plurality of rod-receiving devices, the rod-receiving devices are rarely oriented in a perfectly linear position. More particularly, the varying size of adjacent vertebrae and the often mis-alignment of vertebrae cause the rod receiving devices placed in substantially consistent portions of the vertebrae structure to not be linearly aligned. Consequently, the surgeon often bends or otherwise manipulates the rod during insertion.

Although conventional prior art pedicle screw systems exist, they lack the features that enhance and or benefit newer, minimally invasive surgery (MIS) techniques that are more commonly being used for spinal surgeries. Conventional pedicle screw systems and even more recently designed pedicle screw systems have several drawbacks. Particularly, a number of conventional pedicle screw systems are rather large and bulky, which may result in unnecessary tissue damage in and around the surgical site when the pedicle screw system is installed during surgery. Additionally, a number of conventional pedicle screw systems have a rod-receiving device that is pre-operatively coupled or attached to the pedicle screw, thereby limiting the options available to a surgeon and results in these systems being more difficult to install and maneuver, particularly in conjunction with an MIS technique. In addition, some of the traditional pedicle screw systems include numerous components that must all be carefully assembled together.

Additionally, traditional pedicle screw systems are configured to receive and securely couple substantially straight rods. That is, traditional pedicle screw systems are not well suited for securely coupling a curved rod due to the varying points of contact of the rod with the pedicle screw if the rod is bent a substantial amount.

SUMMARY

According to one exemplary embodiment, a pedicle screw assembly includes at least one inner member configured to fix the tulip assembly to a head of a bone fixation device via an interference fit and an outer member including at least one engagement surface configured to selectively fix a rod in the tulip assembly via rotation of the outer member.

Additionally, according to one exemplary embodiment, a tulip assembly configured to be coupled to a head of a bone fixation device includes an outer housing member with an upper portion and a lower portion having an internal tapered edge in the lower portion. The exemplary assembly also includes a first inner member disposed in a lower portion of the outer member, the first inner member being elastically expandable to receive a head of a bone fixation device. Additionally, a second inner member is disposed in an upper portion of the outer member; the second inner member being configured to receive either a straight or a curved distraction rod. Specifically, the second inner member is configured to be coupled to the head of a bone fixation device via an interference fit. According to one exemplary embodiment, the first inner member includes an external tapered edge and an internal tapered edge, the external tapered edge being configured to mate with the internal tapered edge of the outer housing member to compress the first inner member.

According to one embodiment compressive forces created by an incline plane as the tulip assembly is rotated cause an interference fit between the tulip assembly and saddle, causing a rod to be frictionally secured. The same forces cause the saddle to be forced against the head of the pedicle screw; thus, the head is secured between the saddle and the lower portion of the tulip assembly and expandable ring.

According to one exemplary method, a pedicle screw is inserted into a desired bone, a tulip assembly is fitted over the head of the pedicle screw, a saddle and rod are placed within the tulip assembly, and by twisting the tulip assembly compression due to an interacting incline plane secure the rod within the tulip assembly and secure the tulip assembly to the head of the pedicle screw at a desired angle.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

Figure 1:
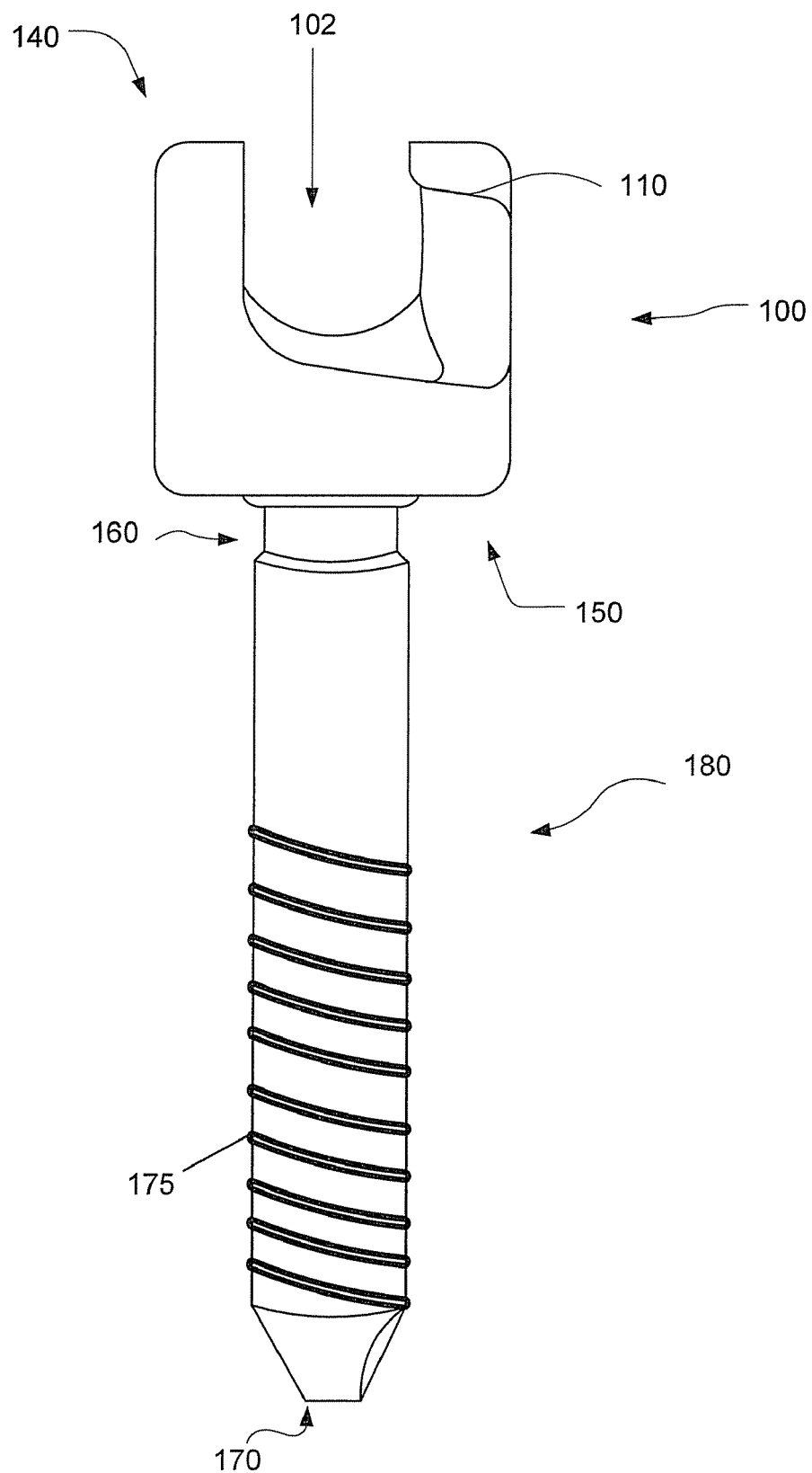
FIG. 1 is a side view of an assembled tulip body attached to a pedicle screw, according to one exemplary embodiment.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification describes a system and a method for provisionally securing a tulip assembly relative to a pedicle screw and then locking a rod within a channel of the tulip assembly. Further, according to one exemplary embodiment, the present specification describes the structure of a tulip assembly configured to be placed on the head of a pedicle screw after securing a pedicle screw in the bone of a patient's body. The present exemplary system and method is configured to receive and positionally secure either a curved or straight top loaded rod. Details of the present exemplary system and method with reference to the figures will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate at least portions of the spine. Examples of desired manipulation are correcting curvature, compression, expansion, structural reinforcement, or other desired manipulations to the bones segments. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod coupling assembly (herein after referred to as a tulip assembly or a tulip body). This is advantageous because the surgeon often needs to do other inter-body work after inserting the pedicle screw, but before attaching the larger and bulkier tulip assembly. Such an advantageous pedicle screw system may be even more crucial when using MIS techniques because the interbody spatial boundaries in which the surgeon must work may be quite limited.

In addition to accommodating the MIS approach to lumbar fusion, poly-axial pedicle screw systems, in accordance with several embodiments of the present exemplary system and method, remedy problems prevalent in traditional systems. First, 'tulip splaying', which is a post-operative problem of a stressed rod forcing open the tulip and thus disassembling the implanted poly-axial pedicle screw construct, is eliminated. Second, pain due to soft-tissue irritation from bulky or high profiled systems is reduced or eliminated. Additionally, the process of securing the rod within the tulip body is also greatly simplified.

Further, pedicle screw systems in accordance with several embodiments of the present exemplary system and method advantageously allow a user to initially lock the tulip assembly relative to the pedicle screw at a desired angle before fully locking the rod, thereby facilitating compression and distraction of the spinal segments. Initially locking the tulip assembly to the pedicle screw means that at least one of the components of the tulip assembly is manipulated to grip and/or clamp onto the pedicle screw to reduce any translational and/or rotational movement of the tulip assembly relative to the pedicle screw. The ability to initially lock the tulip assembly to the pedicle screw may facilitate the surgeon in performing compression and/or distraction of various spinal and/or bone sections.

Another advantageous feature of at least one embodiment of the present exemplary system and method is that a tulip assembly can be coupled to the head portion of the pedicle screw intra-operatively. That is, the present exemplary tulip assembly may include features that enable the tulip assembly to be provisionally locked onto the head portion of the pedicel screw and then to further finally lock the rod within the tulip assembly in-situ. In one exemplary embodiment, the present exemplary tulip assembly decreases the complexity of the pedicle screw system installation by reducing the installation to essentially a seven-step process namely, inserting a pedicle screw into a desired bone location, placing tulip assembly over the head of the pedicle screw, inserting a saddle within the tulip assembly, inserting and seat a rod within the tulip assembly in the saddle, compressing the saddle to lock the tulip assembly to the pedicle screw, compressing or distracting spinal segments, and rotating the tulip assembly to secure the rod within the tulip assembly.

In addition to accommodating an MIS approach to spinal correction and/or fusion, the present exemplary system and method are configured to eliminate instances of cross-threading and/or post-operative splaying, which occurs when the amount of stress or strain in a rod, which may be caused by post operative back flexion forces, opens the tulip assembly and eventually leads to the disassembly and/or the failure of the pedicle screw system. Cross threading is prevented as no threads are used to secure the rod or the tulip assembly and a tendency to splay is reduced as the forces securing both the rod and the tulip assembly are in a downward direction.

In the following description, certain specific details are set forth in order to provide a thorough understanding of various embodiments of the present pedicle screw assembly. However, one skilled in the relevant art will recognize that the present exemplary system and method may be practiced without one or more of these specific details, or with other methods, components, materials, etc. In other instances, well-known structures associated with pedicle screw assemblies have not been shown or described in detail to avoid unnecessarily obscuring descriptions of the present exemplary embodiments.

As used in the present specification, and in the appended claims, the term "ring" or "expansion ring" shall not be interpreted as necessitating a circular cross section. Rather, as used herein and in the appended claims, the term "ring" or "expansion ring" may include any object having a substantially closed periphery regardless of the cross-sectional profile, including embodiments with expansion gaps or other slight variations in the periphery of the object. The term "ring" shall include objects having flat-sided profiles, curvilinear profiles, and/or profiles defined by a varying radius.

The term "distraction," when used herein or in the appended claims, and when used in a medical sense, generally relates to joint surfaces and suggests that the joint surfaces move perpendicular to one another. However when traction and/or distraction is performed, for example on spinal sections, the spinal sections may move relative to one another through a combination of distraction and gliding, and/or other degrees of freedom.

Furthermore, as used in the specification and the appended claims, the terms "interference fit" and "press fit" shall be used interchangeably to describe the insertion of one member into another whose diameter is slightly smaller than the part being inserted.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

FIG. 1 is a side view of a tulip body (100) attached to a pedicle screw (180), according to one exemplary embodiment. As is illustrated in FIG. 1, and is further clarified in subsequent drawings, the tulip body consists of a distal end (150) and a proximal end (140). The distal end being configured to receive and secure the head (not shown) of a pedicle screw (180) near the proximal end (160) of the pedicle screw (180). As is shown and will be discussed in detail below, the tulip body contains an access opening (102) on the proximal end (140) allowing a coupling saddle and a rod to be inserted within the tulip body (100). An incline plane (110) disposed on a surface of the tulip body (100) is configured to interact with a rod that has been placed within the tulip body. The incline plane (110) encounters the rod as the tulip body is rotated or twisted relative to the rod, the incline plane will contact the rod and impart a downward force on the rod. The downward force caused by the incline plane will create an interference fit, frictionally securing a rod within the tulip body and causing saddle to frictionally secure the tulip body at an angle relative to the pedicle screw.

The pedicle screw (180) used in the present exemplary system and method may be of any of the various pedicle screws common in the art. According to one exemplary embodiment illustrated in FIG. 1, the exemplary pedicle screw (180) includes a substantially spherical head, a shaft with threads (175) for securing the screw within a bone, and a distal end (170) configured to penetrate and facilitate insertion of the pedicle screw into the desired bone.

Figure 2:
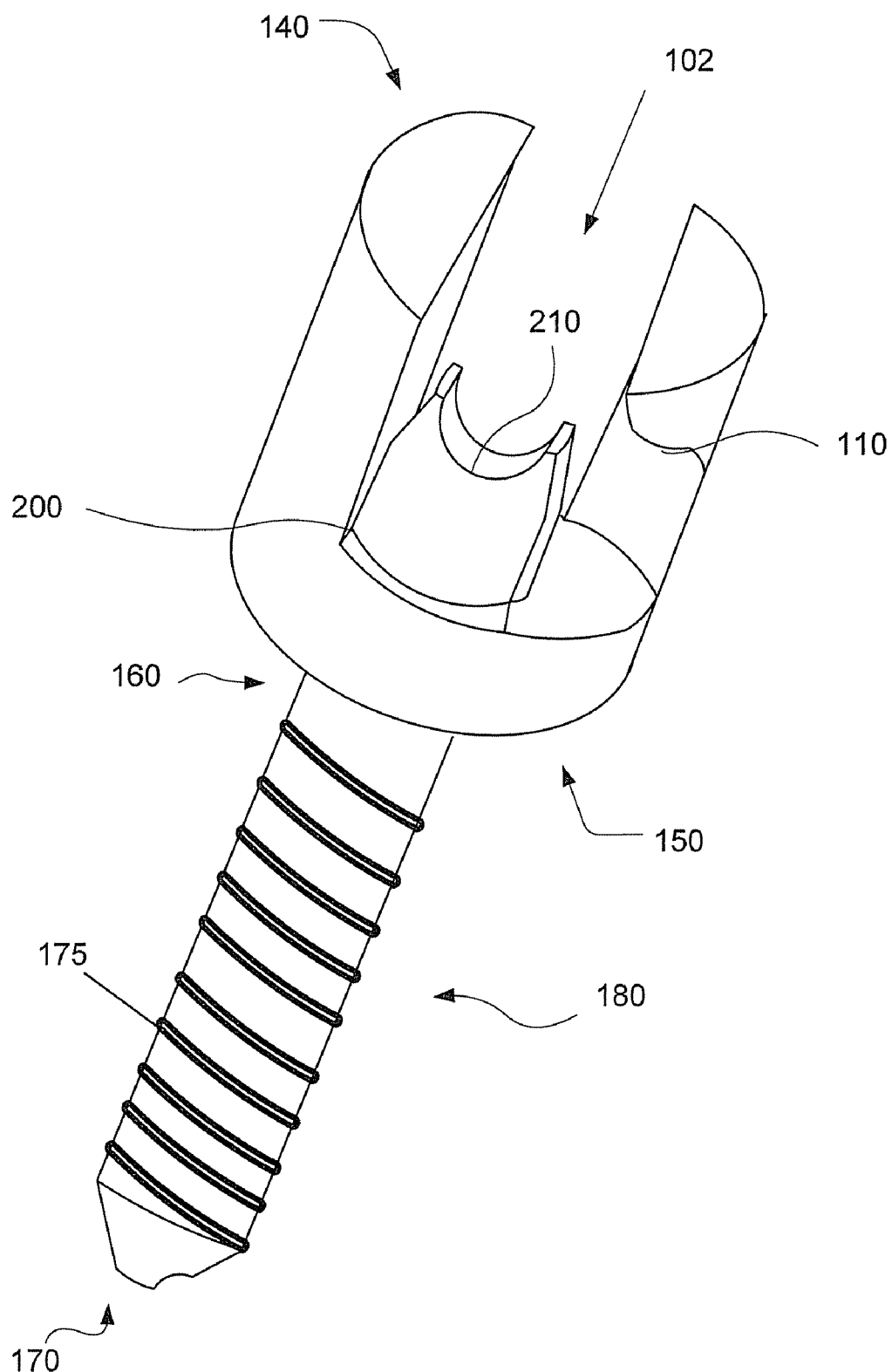
FIG. 2 is a perspective view of a tulip assembly and saddle coupled to a pedicle screw, according to one exemplary embodiment.

FIG. 2 illustrates a perspective view of an exemplary tulip assembly or tulip body (100) secured to a pedicle screw (180), according to one embodiment. As illustrated in FIG. 2, a coupling saddle (200) has been placed within the access opening (102) of the tulip body (100) and is now seated against the head (not shown) of the pedicle screw (180). As illustrated in FIG. 2, the coupling saddle (200) has a generally cylindrical shape including at least one extension proximally protruding from the main body defining a rod receiving channel (210). Additionally, an inner bore is formed in a distal end of the main body of the coupling saddle (200) for securely coupling the head of the pedicle screw (180). In this exemplary perspective view, the incline plane (110) formed on the upper portion of the tulip body (100) can be seen more clearly. The purpose and operation of the inclined plane (110) will be described in detail below. Further details of the exemplary structure and configurations of the same will be provided below with references to FIGS. 3 through 8.

Figure 3:
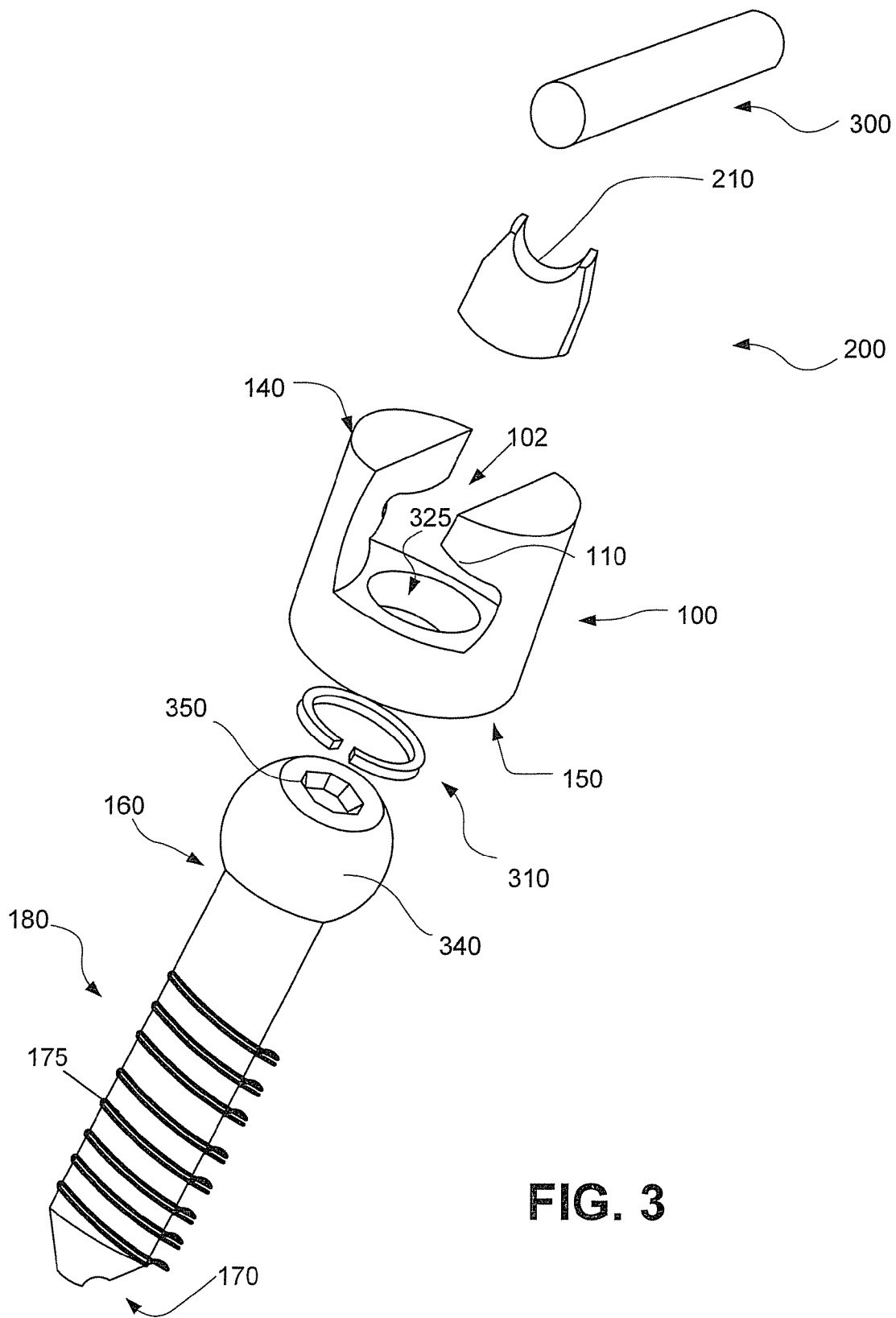
FIG. 3 is a top view of an exploded view of a pedicle screw and tulip assembly, according to one exemplary embodiment.

Continuing with the figures, FIG. 3 is an exploded perspective view of a complete tulip assembly, according to one exemplary embodiment. As shown in FIG. 3, the exploded members illustrate characteristics of the various members inserted in the tulip assembly. For example, as described above, the tulip assembly may be configured to mate with any number of pedicle screws known in the art. However, for ease in explanation only, the present system and method will be described in detail below with reference to a pedicle screw (180) including a driving point or distal end (170), a threaded portion (175) for securing the pedicle screw within a bone, and a head (340) containing driving features (350).

FIG. 3 also illustrates an expansion ring (310) configured to interact with the head (340) of the pedicle screw (180) and the distal end (150) of the tulip body (100) to secure the tulip assembly to the head of the screw. Specifically, according to one exemplary embodiment, the tulip body (100) is configured with a thru bore (325) through which a portion of the head (340) of the pedicle screw (180) passes. As the pedicle screw head (340) enters the thru bore (325) of the tulip body (100) the diameter of the expansion ring (310) is smaller than the largest diameter of the entering pedicle screw head (340). As the pedicle screw head (340) enters the thru bore (325) the expansion ring is forced partially open within the opening (102) of the tulip body (100). The thru bore (325) of the tulip body (100) is configured in such a way so as to accommodate the head of the pedicle screw (340) and allow the expansion ring (310) to expand and then secure the head of the pedicle screw (340) within the tulip body (100). One exemplary embodiment of a thru bore (325) including a seating taper configured to capture a head of a pedicle screw using an expansion ring will be described in further detail below with reference to FIGS. 7A and 7B.

Figure 4:
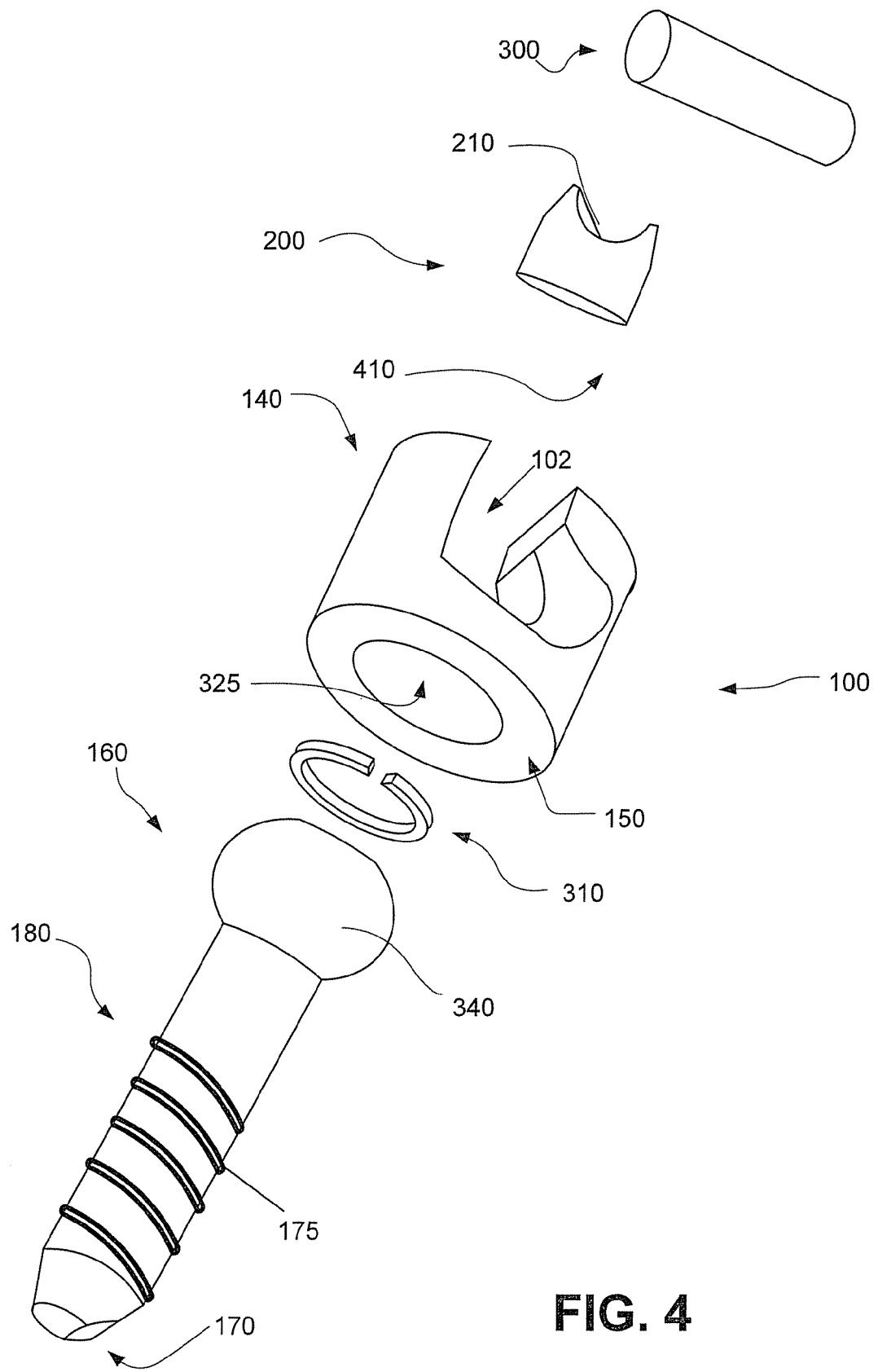
FIG. 4 is a bottom view of an exploded view of a pedicle screw and tulip assembly, according to one exemplary embodiment.

Returning again to FIG. 3 the tulip body includes an opening (102) near the proximal end (140) of the tulip body. The exemplary opening (102) illustrated in FIG. 3 is configured to allow a coupling saddle (200) to be placed within the tulip assembly. The coupling saddle (200), as will be described in greater detail in conjunction with FIG. 4, provides a means to secure the head of the pedicle screw (340), as well as providing a seat for the rod (300). Once in place, the rod (300) can be seated within the tulip body (100) and seated within the rod-receiving channel (210) of the coupling saddle (200). By imparting a downward force on the rod (300), the coupling saddle (200) is pushed against the head of the pedicle screw (340) and acts to secure the tulip body (100) at a relative angle to the pedicle screw (180). Furthermore, as will be described in greater detail below, the tulip body (100) may be rotated with respect to the other members of the tulip assembly causing an incline plane (110) to interact with the rod (300). As the tulip body (100) is rotated to a maxim, the rod (300) contacts the sidewall of the tulip body (100) and the incline plane (110) imparts a downward force on the rod (300). The various members of the tulip assembly and pedicle screw including: the incline plane (110), the rod (300), a coupling saddle (200), a pedicle screw head (340), an expansion ring (310), and a bottom part of the distal portion of the tulip body (100), are all held in an interference fit. This frictional interference fit results in the rod (300) being secured within the tulip body (100) and the tulip assembly is held and secured at a desired angle relative to the pedicle screw (180).

FIG. 4 is an exploded view of a complete tulip assembly, according to one exemplary embodiment. FIG. 4 is a bottom perspective view of the exploded members illustrating characteristics of the various members comprising the tulip assembly found on the lower portions of those members. The exemplary embodiment illustrated in FIG. 4 is configured to be assembled in a similar manner as that described above in conjunction with FIG. 3. Consequently, some details will not be repeated so as to highlight the importance of features shown in FIG. 4 that are not shown as well in FIG. 3.

Of note in the exploded view of FIG. 4, the bottom thru bore (325) of the tulip body (100) can be seen as well as the bottom opening (410) of the coupling saddle (200). As illustrated, the thru bore (325) of the tulip body (100) includes an inner wall configured to receive an expansion ring (310) and secure the head of a pedicle screw (340). Details of the inner walls of the thru bore (325) are not illustrated in FIG. 4, but will be shown in greater detail in conjunction with the cross sectional view of subsequent figures.

The exemplary coupling saddle (200) illustrated in FIG. 4 is a generally cylindrical member including a rod receiving channel (210) on a first side and an orifice or opening (410) on a second side. According to one exemplary embodiment, the illustrated opening (410) is configured to receive the head (340) of the pedicle screw (180) after it has passed through the thru bore (325) and been secured within the thru bore (325) of the tulip body (100) with an expansion ring (310). According to one exemplary embodiment, the opening (410) formed in the coupling saddle (200) is configured to receive, at least partially, the head of the pedicle screw (340) and, as the coupling saddle (200) is forced downward as described above, provide a force on the head of the pedicle screw (340) sufficient to lock the angle of the tulip body (100) relative to the pedicle screw (180).

As shown in both FIG. 3 and FIG. 4, the expansion ring (310) is illustrated as being substantially circular but not forming a closed ring, according to one embodiment. Alternatively, the expansion ring (310) may include any number of expansion reliefs and allow the ring to be of varying shapes and sizes, where the ring may form a closed circular shape or an open ring with an expansion gap as illustrated.

Figure 5A:
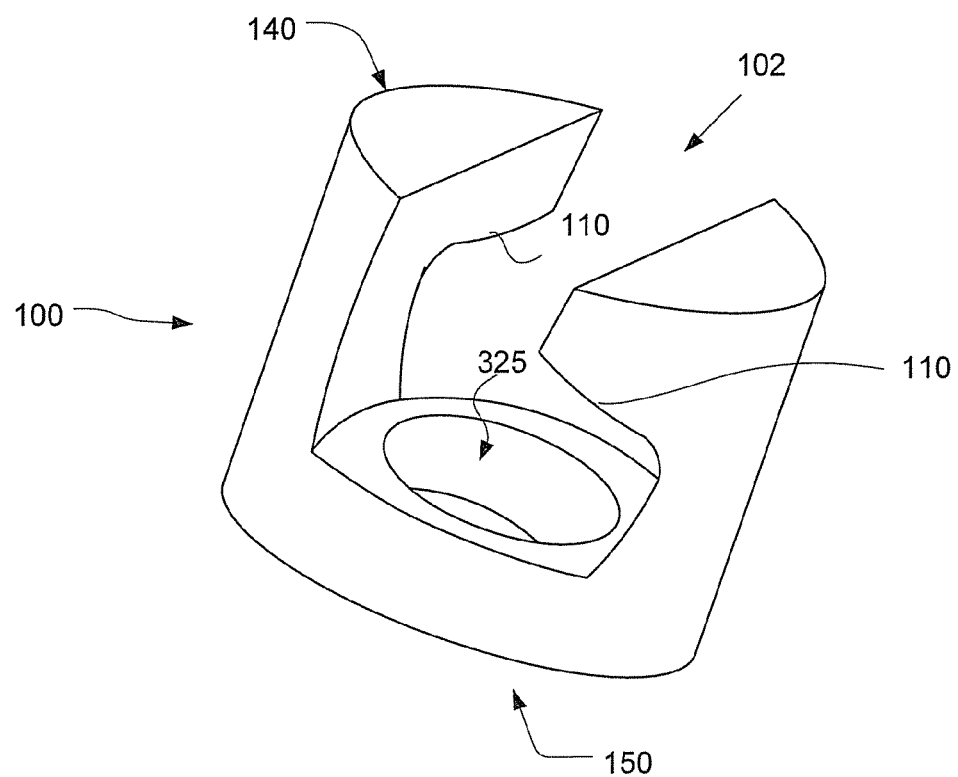
FIGS. 5A and 5B are perspective views of a tulip body, according to one exemplary embodiment.
Figure 5B:
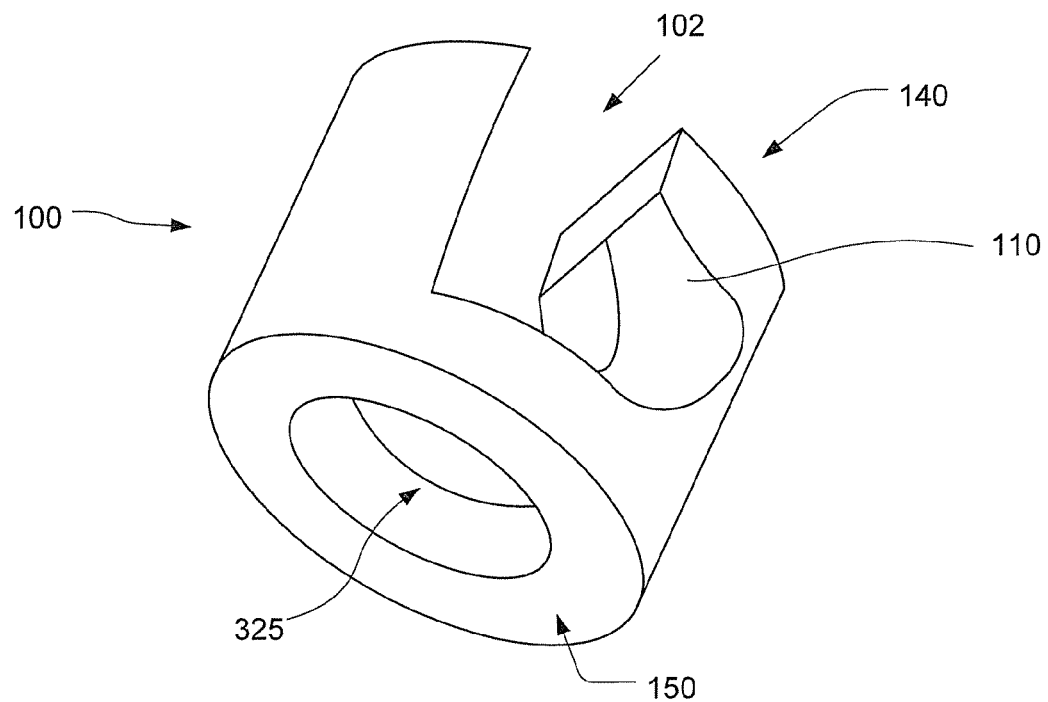

FIGS. 5A and 5B are a top perspective view and a bottom perspective view illustrating exemplary embodiments of the tulip body. As can be seen in the figures, an access opening (102) is formed on the proximal end (140) of the tulip body (100) and a thru-bore (325) is formed on the distal end (150). According to one exemplary embodiment, the access opening (102) is sized and otherwise configured to allow the coupling saddle (200, FIG. 3) and the rod (300, FIG. 3) to be placed within the tulip body (100). Similarly, the exemplary thru-bore (325) is sized so as to allow the head of a pedicle screw to pass there through and become captured by the tulip body (100), due in part according to one exemplary embodiment to an expansion ring interacting with features formed on the inner surface of the tulip body (100) defined by the thru-bore (325).

Of particular note in FIGS. 5A and 5B, the incline plane (110) is clearly illustrated. As shown in FIG. 5A, the exemplary tulip body (100) has two incline planes (110), one on each side of the access channel (102). The incline planes are of importance because, as described above, they act upon the rod (300, FIG. 3) forcing the rod downward when the tulip body is rotated. Specifically, as the tulip body (100) is rotated relative to the other members, such as the rod, saddle, and the pedicle screw, the incline planes will come into contact with the rod (300, FIG. 3) and force the rod down against the saddle (200, FIG. 3). According to one exemplary embodiment, the downward force imparted on the saddle (200; FIG. 3) will cause the bottom opening (410, FIG. 4) of the coupling saddle (200, FIG. 4) to engage the head of the pedicle screw (340, FIG. 4) via an interference fit. When the tulip body (100) is fully rotated, the tulip body (100) is secured at a desired angle relative to a pedicle screw, and a rod is positionally secured within the tulip body (100).

While the above-mentioned description has been provided within the context of a straight rod having a single diameter, a rod may be of varying diameters and/or may be curved or straight according to the application. The present exemplary tulip assembly is able to accommodate both rods of varying diameters as well as curved rods. Particularly, the present exemplary system and method is able to receive rods having varying diameters and curved rods without modification to the design. According to one exemplary embodiment, the size of the rod determines how far down the saddle (200) is pushed against the head (340) of a pedicle screw (180). In other words, variations of the diameter of the rod used or a curve or other non-linear variation of the rod merely vary the linear travel of the saddle (200) along the head (340) of the pedicle screw (180) as an interference fit is created. According to one exemplary embodiment, the internal diameter of the thru-bore (325) is substantially consistent, maintaining a substantially consistent interference fit with the head portion of the pedicle screw (180) regardless of the amount of travel by the saddle (200). By designing the saddle (200) in such a way so as to allow the saddle to form a proper interference fit with the head of the pedicle screw (180) in multiple linear positions, various rods of various shapes may be placed within the assembly.

Figure 6:
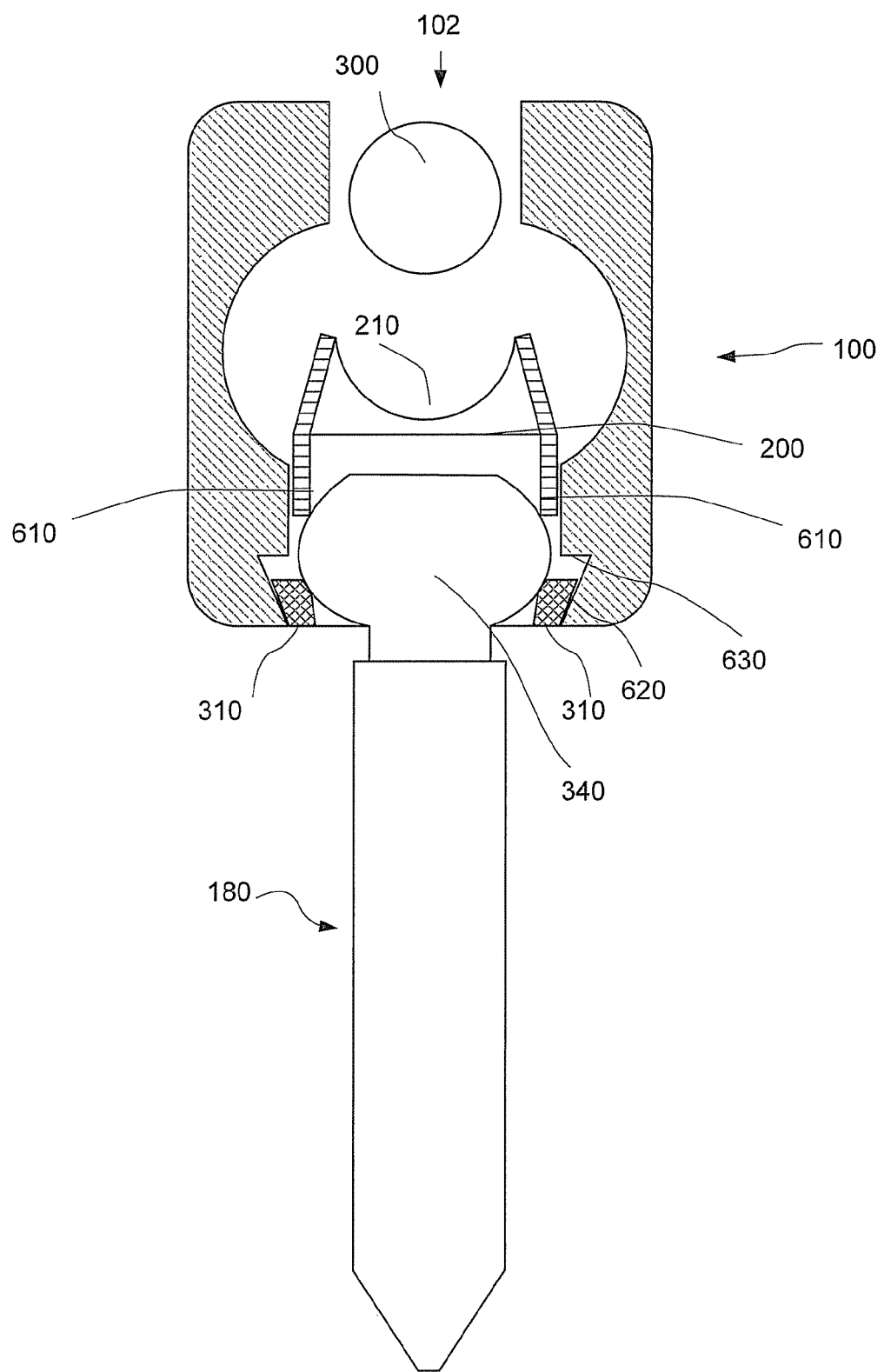
FIG. 6 is a cross sectional view of a tulip assembly and pedicle screw prior, according to one exemplary embodiment.

FIG. 6 illustrates a cross-sectional view of an assembled pedicle screw system according to one exemplary embodiment. According to the illustrated cross-sectional view, the pedicle screw (180), the tulip body (100), the expansion ring (310), the rod (300), and the saddle (200) are positioned to interact upon the insertion of the rod. As can be seen in FIG. 6, a pedicle screw (180) has a head (340) that is placed within the tulip body (100), a cross sectional view of the expansion ring (310) shows how the expansion ring (310) has already expanded and subsequently contracted around the lower portion of the pedicle screw head (340).

As mentioned previously, the expansion ring (310) is sized and configured to be received and retained in the lower portion of the tulip body (100). Accordingly, a number of features are formed on the expansion ring (310) to facilitate both the insertion of the expansion ring (310) into the tulip body (100) and to allow the expansion ring (310) to receive the head portion of the pedicle screw (180) while aiding in locking the relative angular position of the tulip body.

Specifically, as illustrated, the exemplary expansion ring (310) includes a main member body having an expansion gap formed therein. According to one exemplary embodiment, the expansion gap is configured to facilitate the expansion and contraction of the expansion ring (310) without causing undue stresses on the member material. In addition to the expansion gap, the expansion ring (310) may include a lower head receiving orifice.

Additionally, as illustrated in FIG. 6, the thru-bore (325) includes an expansion ring retention lip (630) and a seating taper bore (620) defined therein. According to one exemplary embodiment, the expansion ring (310) interacts with the expansion ring retention lip (630) to provide a resistance to translation of the expansion/contraction member during the insertion of the head portion (340) of the pedicle screw (180). Additionally, according to one exemplar embodiment, the expansion ring (310) includes a seating taper that coincides with the taper bore (620) of the tulip body (100). According to one exemplary embodiment, the seating taper is configured to be positioned within the taper bore (620) and create a mechanical advantage sufficient to lock the relative angular position of the tulip body (100) with respect to the pedicle screw (180). Particularly, the seating taper of the expansion ring (310) frictionally contacts the taper bore (620) of the tulip body (100). Simultaneously, the expansion ring (310) frictionally engages the head portion (340) of the pedicle screw (180), as will be described in more detail below.

With the expansion ring (310) seated in the taper bore (620), the head portion (340) of the pedicle screw (180) is securely fastened within the thru-bore (325, FIG. 5) in the tulip body (100). It can also be seen in FIG. 6 that the coupling saddle (200), when assembled is configured to interact with the head portion (340) of the pedicle screw (180). Particularly, as illustrated in the cross-sectional view of FIG. 6, the saddle wall (610), having a substantially consistent diameter, is configured to slideably engage the head of the pedicle screw (340) to form an interference fit. When a downward force is imparted on the rod, the saddle wall (610) is forced down, which in turn causes the head (340) to be forced against the expansion ring (310) and the tulip body (100). With sufficient force, such as the force applied by the incline planes when the tulip body is rotated, the saddle wall (610) and the expansion ring (310) frictionally secure the head of the pedicle screw, locking it from axial rotation.

FIG. 6 illustrates how a rod (300) may be placed within the access opening (102), according to one exemplary embodiment. As illustrated, the rod (300) is passed through the access opening (102) and subsequently seated on the coupling saddle (200) in the rod-receiving channel (210). As the tulip body (100) is rotated, the internal rod (300) and saddle (200) would be forced down against the pedicle screw head (340) with the expansion ring (310) providing an equal and opposite force, thereby securing the rod (300) within the tulip assembly (100) as well as fixing a relative angle between the tulip assembly (100) and the pedicle screw (180).

Figure 7A:
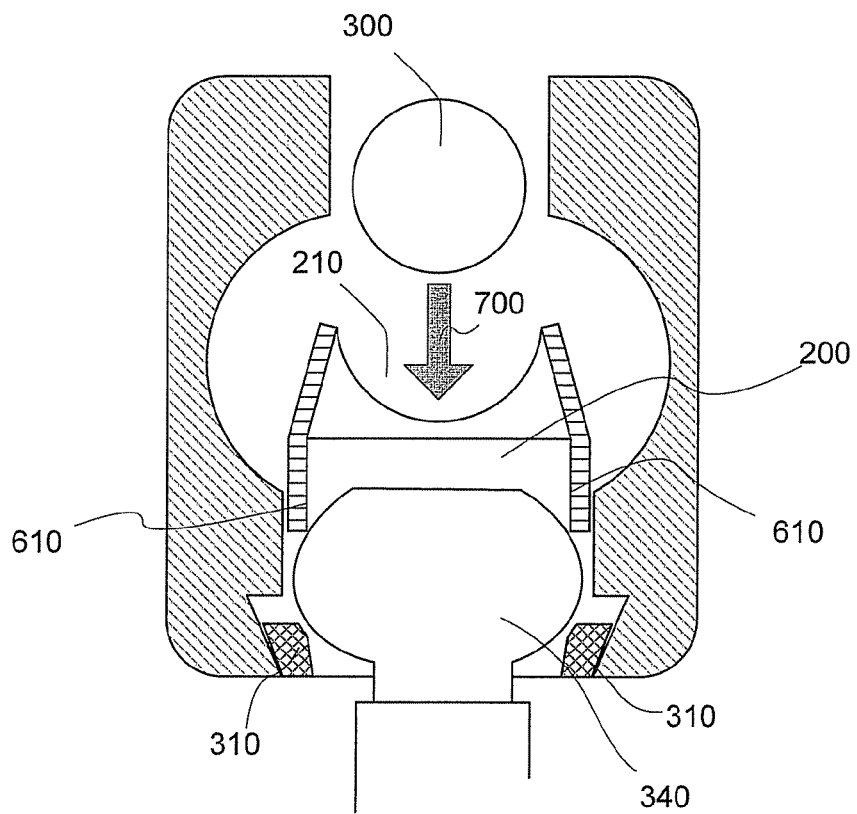
FIG. 7A is a partial cross sectional side view of a tulip assembly and pedicle screw prior to the saddle being provisionally secured to the head of the pedicle screw, according to one exemplary embodiment.
Figure 7B:
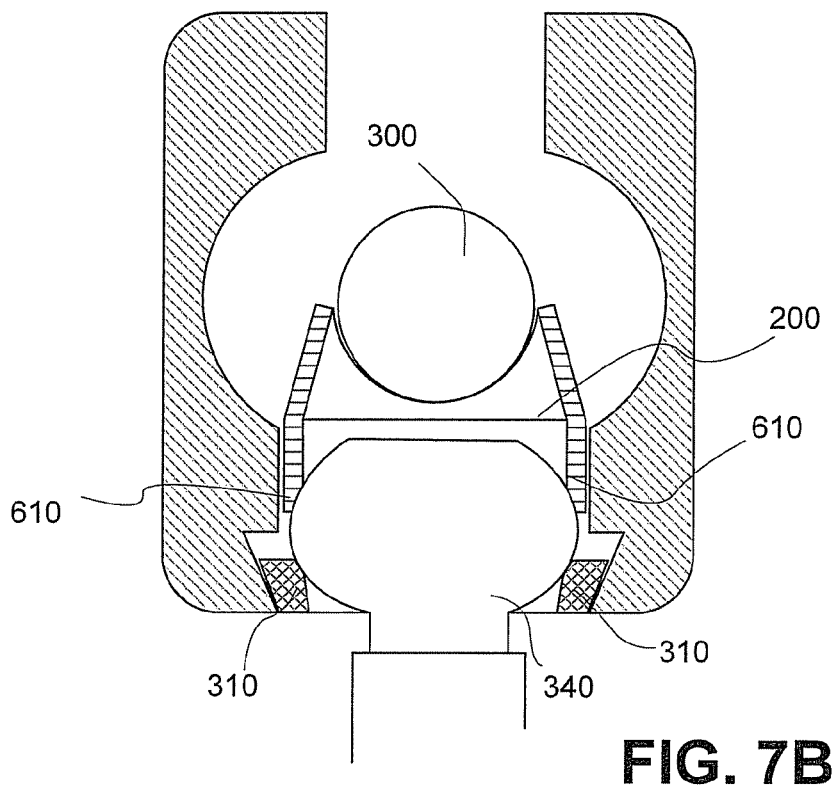
FIG. 7B is a partial cross sectional view of a tulip assembly provisionally secured to the head of a pedicle screw, according to one exemplary embodiment.

FIGS. 7A and 7B are provided in order to illustrate the provisional locking of a pedicle screw relative to a tulip body, according to one exemplary embodiment. As illustrated in FIG. 7A, the present exemplary system is assembled including a coupling saddle (200) with a saddle wall (610) contacting a head of a pedicle screw (340). When initially assembled, there is no downward force exerted on the coupling saddle. Furthermore, during initial assembly, as can be seen in FIG. 7A, the expansion ring (310) is in place within the thru-bore, but is not interacting with the pedicle screw head (340), nor is the expansion ring (310) creating a force by which to secure the pedicel head (340). With the insertion of a rod (300), a downward force (700) may be applied to the saddle. Specifically, according to one exemplary embodiment, as the rod (300) is inserted and seated into the coupling saddle (200), a force (700) is applied. The force (700) is translated through the rod and to the coupling saddle (200). According to one exemplary embodiment, by applying the insertion force (700) on the rod (300), the coupling saddle (200) engages the pedicle screw head (340) and initiates an interference fit.

After the downward force (700) is applied, a provisional lock is established, as illustrated in FIG. 7B, according to one exemplary embodiment. As shown, once the saddle (200) is translated downward relative to the pedicle screw head (340), the saddle wall (610) is forced against the head of the pedicle screw (340). According to one exemplary embodiment, sufficient force is applied to cause the head of the pedicle screw (340) to engage the expansion ring (310). The downward force caused by the saddle walls (610) and the upward force caused by the expansion ring (310) secure the pedicle screw head (340) in a frictional interference fit within the saddle, preventing the screw head (340) from freely moving relative to the tulip body (100). However, the provisional interference fit is not a fully locked position, thus the tulip body (100) may still be rotated, with the application of increased force compared to the unlocked position, into a desired position, after which the assembly is fully locked. A provisional lock allows the operator to manipulate other features without worry of the tulip body (100) freely moving relative to the pedicle screw (180, FIG. 6); while a fully locked position secures the tulip body (100) to the pedicle screw (180) without unintended motion or slipping.

Figure 8A:
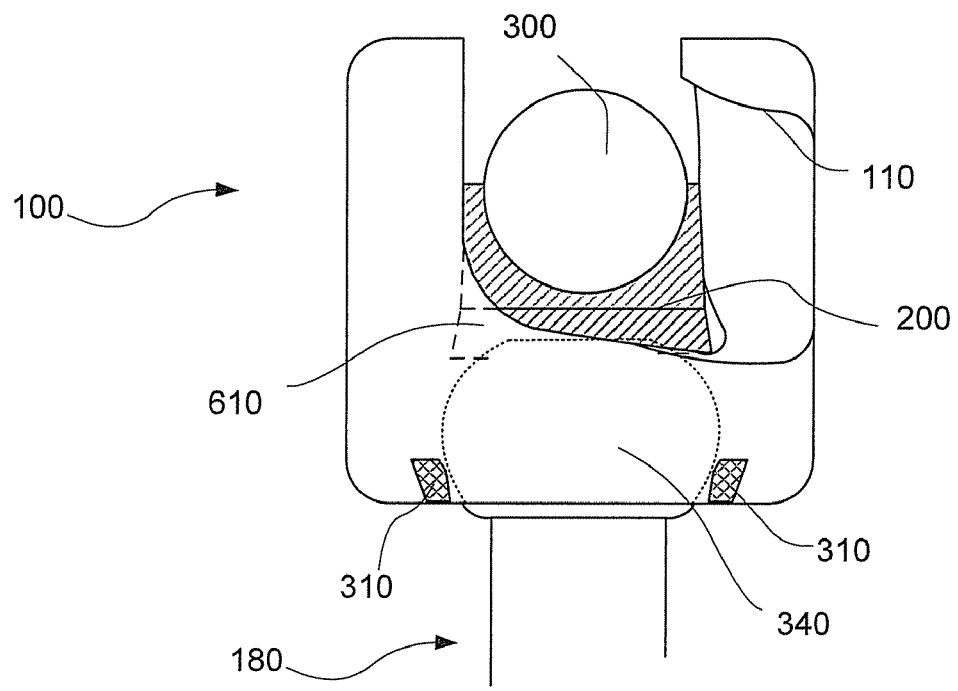
FIG. 8A is a side view illustrating a tulip assembly provisionally secured to a pedicle screw, according to one exemplary embodiment.
Figure 8B:
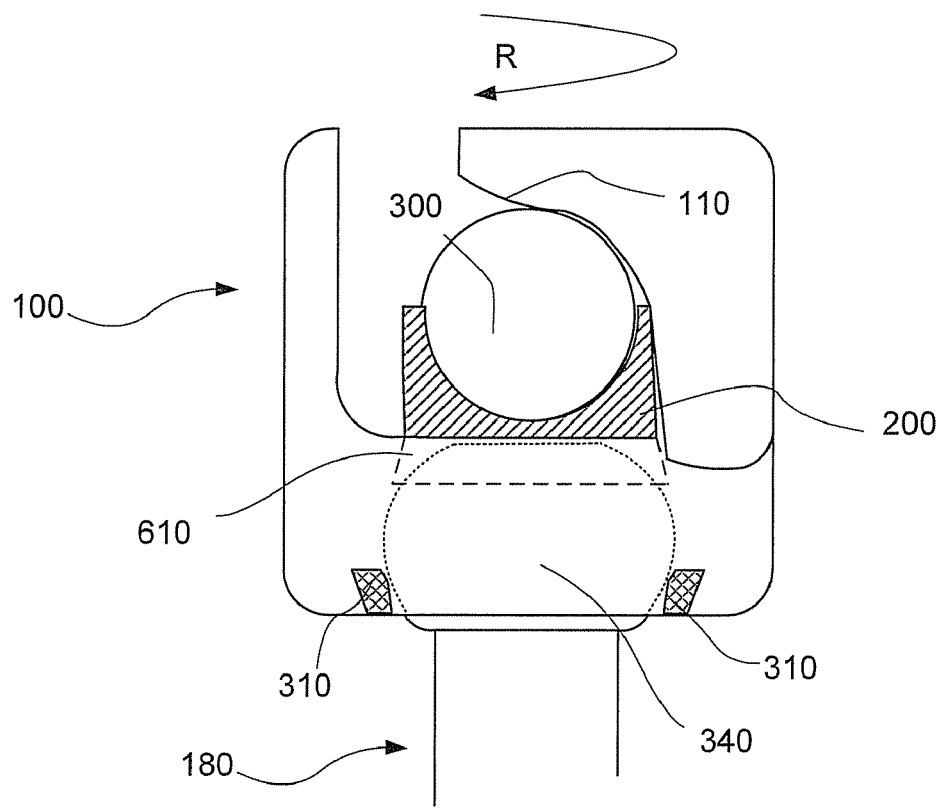
FIG. 8B is a side view illustrating a rod captured by the tulip assembly, an incline plane provides a frictional force sufficient to secure the rod within the channel and fix the tulip assembly to the head of the pedicle screw, according to one exemplary embodiment.

FIG. 8A illustrates a partial cross-sectional view of the present exemplary system including a rod (300) inserted into the tulip body (100) and oriented in a provisionally locked position, according to one exemplary embodiment. As illustrated in FIG. 8A, a coupling saddle (200) has been placed within the tulip body (100) along with a rod (300). A downward force has been applied to the rod (300), causing the rod to be seated within the coupling saddle (200) and initiating an engagement between the coupling saddle (200) and the pedicle screw head (340). As illustrated in FIGS. 8A and 8B, dashed lines are used to show internal features of components of the assembly and may be useful in visualizing the locking method. It can be seen in FIG. 8A that the coupling saddle (200) is provisionally locked to the head of the pedicle screw (340), it has been forced downward sufficient to cause the head (340) to be frictionally secured between the saddle (200) and the expansion ring (310). Consequently, the assembly (100) is in a provisionally locked position. Furthermore, as illustrated in FIG. 8A, when the present exemplary system and method are in a provisionally locked state, the tulip body (100) has not been rotated and the incline plane (110) formed on the tulip body (100) is not interacting with the rod (300).

In contrast to FIG. 8A, FIG. 8B illustrates the final locking of the present exemplary system. As can be seen in FIG. 8B, according to one exemplary embodiment, the tulip assembly may be rotated, as shown by the rotating arrow (R). As the tulip assembly (100) is rotated the incline plane (110) comes into contact with the rod (300). Further rotation of the tulip assembly (100) advances the incline plane (110) relative to the rod (300), thereby forcing the rod downward. Further advancement of the rod due to the rotation (R) of the tulip assembly causes the coupling saddle (200) to transfer a greater force against the head of the pedicle screw (340) further advancing the pedicle screw head (340) into the dashed internal view of the coupling saddle (200) than established during the provisional lock illustrated in FIG. 8A. The added downward force caused by the interaction between the incline plane (110) and the rod (300) is sufficient to securely lock the pedicle screw (180) to the tulip assembly (100). As mentioned previously, any number of rods having varying diameters and/or bends can be employed by the present exemplary configuration. Bent rods and/or rods having varying diameters will merely vary the degree of advancement of the coupling saddle (200) relative to the pedicle screw head (340), each varying degree establishing a sufficient interference fit to establish a final lock.

As shown in FIG. 8B, an exemplary relative angle between the pedicle screw (180) and the tulip body (100) is shown. However, it is possible to secure the tulip body (100) at various axial angles relative to the pedicle screw (180). According to one exemplary embodiment, the incline planes are configured with protrusions or a pronounced recess at the final locked position. According to this exemplary embodiment, the protrusions or pronounced recess establish a fully locked position and prevent the tulip body from unintentionally rotating back from a fully locked position and releasing the rod.

Exemplary Method

Figure 9:
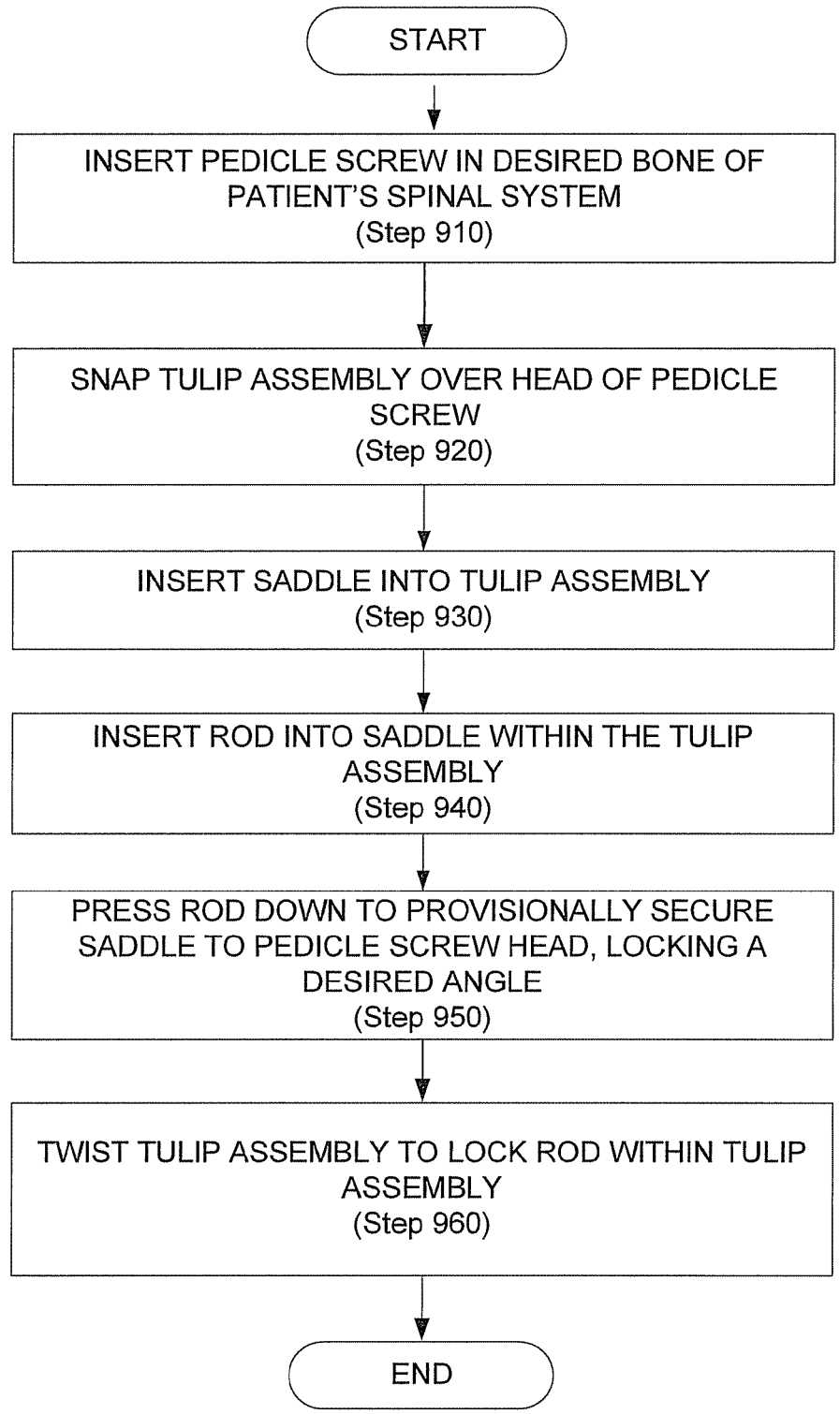
FIG. 9 is a flowchart of a method of installing a pedicle screw and subsequent securing of a rod within the tulip assembly secured to the pedicle screw, according to one exemplary embodiment.

A method of securing a rod within a tulip assembly attached to a bone by a pedicle screw is shown in FIG. 9, according to one exemplary embodiment. As illustrated in FIG. 9, the present exemplary method is initiated by inserting a pedicle screw into the bone of a patient in a desired location (step 910). According to one exemplary embodiment, one or more pedicle screw may be inserted in a patient's spinal system corresponding to a desired number of pedicle screw and tulip assembly systems. The placement and/or number of pedicle screw and tulip assembly systems to be used in a patient may be pre-operatively determined based on a pre-operative examination of the patient's spinal system using non-invasive imaging techniques known in the art, such as x-ray imaging, magnetic resonance imaging, and/or fluoroscopy imaging. Any additional preparation or work can be performed in order to ensure that the screw is firmly implanted in the proper location in the patient for the particular spine surgery being preformed.

Referring to FIG. 3 for component references, once the pedicle screws are properly placed (step 910), a tulip body (100, FIG. 3) is then placed over the head of the pedicle screw (step 920). As described in detail above, the present exemplary tulip body (100) includes an expansion ring (310) in the thru-bore (325) configured to receive the insertion of a head portion (340) of a pedicle screw (180) and then contract to secure the head portion (340) of the pedicle screw (180) within the tulip body (100). This exemplary configuration permits intra-operative insertion of the tulip body (100) onto the head portion (340) of the pedicle screw (180). The tulip body (100) is effectively "snapped" into place on the head of the pedicle screw (340).

According to one exemplary embodiment, when the tulip assembly (100) is snapped onto the head portion (340) of the pedicle screw (180), the lower head interfacing surface of the expansion ring (310) mates with the head portion (340) of the pedicle screw (180). As the tulip assembly (100) is pushed onto the head portion (340) of the pedicle screw (180), the expansion ring (310) expands and snaps on the head portion (340). The expansion ring (310) is initially pushed up into the bore (325) of the tulip body (100), as previously described. The bore (325) in the distal end (150) of the tulip body (100) permits the expansion ring (310) to float in the bore (325) until it makes contact with a ring expansion channel. Alternatively, the expansion ring (310) is pushed upwards inside of the tulip body (100) by the head portion (340) of the pedicle screw (180), the expansion ring (310) expands until sufficient clearance is present for the expansion ring (310) to expand and snap around the head portion (340) of the screw (180). At this point of the installation method, the tulip assembly (100) may be rotationally coupled to the head portion (340) of the pedicle screw (180).

Continuing with the present exemplary method, once the tulip assembly is snapped in place, a coupling saddle (200) is inserted into place (step 930). The coupling saddle is placed with distal saddle walls (610, FIG. 6) resting on the head portion (340) of the pedicel screw (180). A rod-receiving channel (210, FIG. 3) defined by the tulip body (100) is oriented such that the rod (300) may be placed within the access opening (102) of the tulip body (100) and seated in the channel (210).

Once the coupling saddle (200) is properly placed (step 930), a rod (300; FIG. 3) is placed within the present exemplary assembly (step 940). According to one exemplary embodiment, the rod is placed through the access opening (102) of the tulip body (100) and is seated in the channel (210) of the coupling saddle (200). With the rod (300) in place, the tulip body (100) may be provisionally secured to the pedicle screw (step 950). As mentioned previously, the rod (300) may be pressed in a downward manner, forcing the coupling saddle (200) down, causing the saddle walls (610, FIG. 6) to be forced against the head portion (340, FIG. 3) of the pedicle screw (180). This interaction causes the head portion (340) of the pedicle screw (180) to be in a provisionally locked configuration. While providing some positional security, the provisionally locked position is not as secure a fit as that of the fully locked position. Again, the provisionally locked state is shown in the cross-sectional view of FIG. 7B Once the tulip assembly (100, FIG. 8A) is provisionally locked to a desired angle relative to the pedicle screw (180), the rod (300) may be secured in the tulip body (100) and the angle between the tulip body (100) and the pedicle screw (180) may be fully locked (step 960). According to one exemplary embodiment, fully locking the angle between he tulip body (100) and the pedicle screw (180) is performed by rotating the tulip body (100, FIG. 8B) relative to the other components comprising the tulip assembly, including the rod (300), saddle (200), and the pedicle screw (180). As is illustrated in FIG. 8B, the rotation of the tulip body (100) causes the incline plane (110) to engage and force the rod (300) down further than it was in a provisionally locked state. The downward force causes the rod (300) to be secured between the two incline planes (110, FIG. 5A and FIG. 8B). Additionally, as illustrated in FIG. 8B, the tulip body (100) is fully locked at an angle relative to the pedicle screw (180) in an interference fit, as described in detail above.

In conclusion, the present exemplary system and method provide for a manner of provisionally securing a tulip assembly relative to a pedicle screw prior to locking a rod within a channel of the tulip assembly. Further, the present exemplary configuration enables the placement of the tulip assembly on the head portion of an installed pedicle screw. Additionally, the present exemplary system and method is configured to receive and positionally secure either a curved or straight top loaded rod without compromise to the positional security of the configuration.

The preceding description has been presented only to illustrate and describe the present method and system. It is not intended to be exhaustive or to limit the present system and method to any precise form disclosed. Many modifications and variations are possible in the light of the above teaching.

The foregoing embodiments were chosen and described in order to illustrate principles of the system and method as well as some practical applications. The preceding description enables others skilled in the art to utilize the method and system in various embodiments and with various modifications, as are suited to the particular use contemplated. It is intended that the scope or the present exemplary system and method be defined by the following claims.

What is claimed is:

1. A tulip assembly configured to be coupled to a head of a bone fixation device comprising:
    at least one inner member configured to fix said tulip assembly to said head of said bone fixation device, wherein said at least one inner member is configured to engage said head of said bone fixation device; and
    an outer member configured to selectively fix a rod in the tulip assembly via rotation of said outer member;
    said bone fixation device comprising a pedicle screw having a threaded portion and said head portion;
    at least a portion of the tulip assembly having generally opposing channels for receiving a rod; said at least a portion of said tulip assembly being adapted to receive said rod and rotate about the rod to capture the rod and cause the rod to become locked in the tulip assembly after said at least one inner member fixes the tulip assembly to the head portion; each of said generally opposing channels being defined by a first surface and a generally opposing second surface, said first and second surfaces also cooperating to define a first channel portion and a second channel portion that is in communication with said first channel portion, said first channel portion defining a rod-receiving opening that opens at an end of said tulip assembly opposite of a second end of said tulip assembly from which said pedicle screw extends, said second channel portion extending about an axis of said tulip assembly.

2. The tulip assembly of claim 1, wherein said first surface defines at least one engagement surface comprising a declining plane configured to force said rod into said at least one inner member when said outer member is rotated.

3. The tulip assembly of claim 1, wherein said at least one inner member comprises:
    a first inner member disposed in a lower portion of said outer member;
    a second inner member disposed in an upper portion of said outer member;
    wherein said first inner member is elastically expandable to receive said head of said bone fixation device; and
    wherein said second inner member is configured to receive said rod and provide an interference fit when said outer member is rotated.

4. The tulip assembly of claim 3, wherein said second inner member comprises:
    a main cylindrical body;
    at least one extension proximally protruding from said main cylindrical body; and
    an inner bore formed in a distal end of said main cylindrical body;
    wherein said inner bore is configured to engage said head of a bone fixation device to create said interference fit between said second inner member and said head of said bone fixation device.

5. The tulip assembly of claim 4, wherein said at least one proximally protruding extension defines a seat configured to receive said rod.

6. The tulip assembly of claim 4, wherein said inner bore comprises a consistent diameter.

7. The tulip assembly of claim 6, wherein said consistent diameter of said inner bore is smaller than an outer diameter of said head of said bone fixation device .

8. The tulip assembly of claim 4, wherein said first inner member comprises a ring configured to be elastically, diametrically expandable and contractible.

9. The tulip assembly of claim 8, wherein said ring includes a split that permits a diameter of the ring to vary from a first, larger diameter to a second, smaller diameter.

10. The tulip assembly of claim 4, wherein said lower portion of said outer member further comprises a seating taper configured to seat said first inner member when a downward force is imparted on said second inner member.

11. The tulip assembly of claim 1, wherein said rod comprises a curved rod.

12. The tulip assembly of claim 1, wherein said rod comprises a rod having a varying diameter.

13. A tulip assembly configured to be coupled to a head of a bone fixation device comprising:
    a first inner member and a second inner member configured to fix said tulip assembly to said head of said bone fixation device; and
    an outer member configured to force said rod into said second inner member when said outer member is rotated;
    wherein said first inner member is disposed in a lower portion of said outer member;
    wherein said second inner member is disposed in an upper portion of said outer member;
    wherein said first inner member is elastically expandable to receive said head of said bone fixation device; and
    wherein said second inner member is configured to receive said rod and advance an engagement of said head when said outer member is rotated;
    said bone fixation device comprising a pedicle screw having a threaded portion and said head;
    at least a portion of the tulip assembly having generally opposing channels for receiving a rod; said at least a portion of said tulip assembly being adapted to receive said rod and rotate about the rod to capture the rod and cause the rod to become locked in the tulip assembly after said first inner member fixes the tulip assembly to the head portion; each of said generally opposing channels being defined by a first surface and a generally opposing second surface, said first and second surfaces also cooperating to define a first channel portion and a second channel portion that is in communication with said first channel portion, said first channel portion defining a rod-receiving opening that opens at an end of said tulip assembly opposite of a second end of said tulip assembly from which said pedicle screw extends, said second channel portion extending about an axis of said tulip assembly.

14. The tulip assembly of claim 13, wherein said second inner member comprises:

a main cylindrical body;

at least one extension proximally protruding from said main cylindrical body; and an inner bore formed in a distal end of said main cylindrical body;

wherein said inner bore is configured to engage said head of a bone fixation device to create an interference fit between said second inner member and said head of a bone fixation device.

15. The tulip assembly of claim 14, wherein said inner bore comprises a consistent diameter.

16. The tulip assembly of claim 15, wherein said consistent diameter of said inner bore is smaller than an outer diameter of said head of a bone fixation device.

* * * * *

UNITED STATES PATENT AND TRADEMARK OFFICE
CERTIFICATE OF CORRECTION

PATENT NO.      : 8,097,025 B2
APPLICATION NO. : 12/056571
DATED           : January 17, 2012
INVENTOR(S)     : David T. Hawkes et al.

Page 1 of 1

It is certified that error appears in the above-identified patent and that said Letters Patent is hereby corrected as shown below:

In Column 5, Line 2, please delete "pedicel" and insert -- pedicle -- therefor.

In Column 9, Line 47, please delete "exemplar" and insert -- exemplary -- therefor.

In Column 10, Line 31, please delete "pedicel" and insert -- pedicle -- therefor.

In Column 12, Line 3, please delete "preformed" and insert -- performed -- therefor.

In Column 12, Line 41, please delete "pedicel" and insert -- pedicle -- therefor.

In Column 13, Line 1, please delete "he" and insert -- the -- therefor.

Signed and Sealed this
Sixteenth Day of October, 2012

David J. Kappos
*Director of the United States Patent and Trademark Office*